United States Patent
Ozinga (10) Patent No.: US 11,571,333 B2
(45) Date of Patent: Feb. 7, 2023

(54) APPARATUS AND METHOD FOR SECURING OCULAR TISSUE AND PROVIDING SURGICAL TOOL POSITIONING POINTS

(71) Applicant: Refocus Group, Inc., Dallas, TX (US)

(72) Inventor: David G. Ozinga, Flower Mound, TX (US)

(73) Assignee: Refocus Group, Inc., Dallas, TX (US)

( * ) Notice: Subject to any disclaimer, the term of this patent is extended or adjusted under 35 U.S.C. 154(b) by 256 days.

(21) Appl. No.: 16/876,642

(22) Filed: May 18, 2020

(65) Prior Publication Data

US 2021/0353457 A1  Nov. 18, 2021

(51) Int. Cl.
| | | |
|---|---|---|
| *A61F 9/00* | (2006.01) | |
| *A61F 9/007* | (2006.01) | |
| *A61B 17/02* | (2006.01) | |
| *A61B 17/30* | (2006.01) | |
| *A61B 17/064* | (2006.01) | |

(Continued)

(52) U.S. Cl.
CPC ........ *A61F 9/0017* (2013.01); *A61B 17/0231* (2013.01); *A61B 17/30* (2013.01); *A61F 9/00781* (2013.01); *A61B 2017/0046* (2013.01); *A61B 2017/00477* (2013.01); *A61B 2017/0649* (2013.01); *A61F 9/0133* (2013.01); *A61F 2220/0008* (2013.01)

(58) Field of Classification Search
CPC ........ A61B 17/0231; A61B 2017/3407; A61B 17/0293; A61F 2009/0052
See application file for complete search history.

(56) References Cited

U.S. PATENT DOCUMENTS

| | | |
|---|---|---|
| 4,124,905 A | 11/1978 | Clark |
| 4,205,682 A | 6/1980 | Crock et al. |
| 4,275,733 A | 6/1981 | Marinoff |

(Continued)

FOREIGN PATENT DOCUMENTS

| | | |
|---|---|---|
| CN | 1043257 A | 6/1990 |
| EP | 0336065 A2 | 10/1989 |

(Continued)

OTHER PUBLICATIONS

"Instruments to help with those frustration situations", Surgical Solutions from Katena, Mar. 2004, 4 pages.

(Continued)

*Primary Examiner* — Thomas McEvoy (57) ABSTRACT

A device includes a body configured to be placed on an eye and multiple tine assemblies configured to secure the body to and release the body from the eye. The body includes multiple corners and multiple sides. Each corner includes a passage through the corner. Each side connects an adjacent pair of corners. Each tine assembly includes a twist pick configured to be inserted through one of the passages. Bottom surfaces of the sides are raised relative to bottom surfaces of the corners such that the bottom surfaces of the sides are spaced apart from the eye when the bottom surfaces of the corners are resting on the eye. Each of at least one side includes multiple openings configured to allow manipulation of a position of the body and a groove configured to receive a projection from a surgical tool in order to position the surgical tool on the eye.

20 Claims, 9 Drawing Sheets

(51) Int. Cl.
    *A61B 17/00* (2006.01)
    *A61F 9/013* (2006.01)

(56) References Cited

U.S. PATENT DOCUMENTS

| | | | |
|---|---|---|---|
| 4,340,059 | A | 7/1982 | Marinoff |
| 4,688,570 | A | 8/1987 | Kramer et al. |
| 4,865,033 | A | 9/1989 | Krumeich et al. |
| 5,002,569 | A | 3/1991 | Lindstrom |
| 5,009,660 | A | 4/1991 | Clapham |
| 5,092,863 | A | 3/1992 | Schanzlin |
| 5,098,443 | A | 3/1992 | Parel et al. |
| 5,437,658 | A | 8/1995 | Muller et al. |
| 5,489,299 | A | 2/1996 | Schachar |
| 6,342,053 | B1 | 1/2002 | Berry |
| 6,527,780 | B1 | 3/2003 | Wallace et al. |
| 6,623,476 | B2 | 9/2003 | Juhasz et al. |
| 6,656,197 | B1 | 12/2003 | LaHaye |
| 6,863,667 | B2 | 3/2005 | Webb et al. |
| 7,087,050 | B2 | 8/2006 | LaHaye |
| 7,189,225 | B2 | 3/2007 | Rosen |
| 7,189,248 | B2 | 3/2007 | Schachar et al. |
| 8,709,029 | B2 | 4/2014 | Griffis, III et al. |
| 9,592,152 | B2 | 3/2017 | Griffis, III et al. |
| 10,744,031 | B2 | 8/2020 | Griffis, III et al. |
| 2002/0103481 | A1 | 8/2002 | Webb et al. |
| 2002/0120285 | A1 | 8/2002 | Schachar et al. |
| 2003/0195622 | A1 | 10/2003 | Hoffmann et al. |
| 2004/0054374 | A1 | 3/2004 | Weber et al. |
| 2004/0073231 | A1 | 4/2004 | Juan, Jr. et al. |
| 2004/0073245 | A1 | 4/2004 | Schachar et al. |
| 2004/0267294 | A1 | 12/2004 | Will |
| 2005/0288697 | A1 | 12/2005 | Tei et al. |
| 2006/0129129 | A1 | 6/2006 | Smith |
| 2006/0241750 | A1 | 10/2006 | Zdenek et al. |
| 2006/0271025 | A1 | 11/2006 | Jones et al. |
| 2007/0162115 | A1 | 7/2007 | Hermeking |
| 2012/0099077 | A1* | 4/2012 | Abt .................... B65D 75/22 351/219 |
| 2012/0226107 | A1* | 9/2012 | Griffis, III ............ A61F 9/007 600/236 |
| 2013/0096386 | A1 | 4/2013 | Christensen et al. |
| 2013/0267988 | A1* | 10/2013 | Sussman ............ A61B 17/0231 606/198 |
| 2014/0052140 | A1 | 2/2014 | Sayegh |
| 2017/0156925 | A1 | 6/2017 | Griffis, III et al. |
| 2018/0206835 | A1 | 7/2018 | Canabrava |
| 2020/0008793 | A1 | 1/2020 | Cote et al. |

FOREIGN PATENT DOCUMENTS

| | | | |
|---|---|---|---|
| EP | 1033120 | A2 | 9/2000 |
| EP | 1099432 | A2 | 5/2001 |
| GB | 1456746 | A | 11/1976 |
| JP | 2000175954 | A | 6/2000 |
| JP | 2000279441 | A | 10/2000 |
| JP | 2001187081 | A | 7/2001 |
| JP | 2002143209 | A | 5/2002 |
| JP | 2003339756 | A | 12/2003 |
| JP | 2004531344 | A | 10/2004 |
| JP | 2006006605 | A | 1/2006 |
| WO | 9114406 | A1 | 10/1991 |
| WO | 9407424 | A1 | 4/1994 |
| WO | 9515120 | A1 | 6/1995 |
| WO | 9528984 | A1 | 11/1995 |
| WO | 0021466 | A1 | 4/2000 |
| WO | 0074600 | A1 | 12/2000 |
| WO | 2006014484 | A2 | 2/2006 |

OTHER PUBLICATIONS

International Search Report and Written Opinion of the International Searching Authority dated Nov. 7, 2008 in connection with International Patent Application No. PCT/US2007/015774, 21 pages.
Annex to Form PCT/ISA/206 Communication Relating to the Results of the Partial International Search dated Apr. 10, 2008 in connection with International Patent Application No. PCT/US2007/015774, 2 pages.
International Search Report and Written Opinion of the International Searching Authority dated Mar. 18, 2009 in connection with International Patent Application No. PCT/US2007/015816, 21 pages.
Extended European Search Report in connection with European Patent Application No. 12172628.5 dated Oct. 19, 2012, 8 pages.
Communication pursuant to Article 94(3) EPC dated Aug. 2, 2011 in connection with European Patent Application No. 07836052.6, 6 pages.
First Office Action dated Aug. 21, 2015 in connection with Canadian Patent Application No. 2,853,984, 4 pages.
Japanese Office Action dated May 15, 2012 in connection with Japanese Patent Application No. 2009-519513, 7 pages.
Office Action dated Nov. 8, 2012 in connection with U.S. Appl. No. 11/827,444, 12 pages.
Office Action dated Jul. 12, 2013 in connection with U.S. Appl. No. 13/413,218, 17 pages.
International Search Report and Written Opinion of the International Searching Authority dated May 6, 2021 in connection with International Patent Application No. PCT/US2021/019233, 10 pages.

* cited by examiner

APPARATUS AND METHOD FOR SECURING OCULAR TISSUE AND PROVIDING SURGICAL TOOL POSITIONING POINTS

TECHNICAL FIELD

This disclosure is generally directed to surgical devices. More specifically, this disclosure is directed to an apparatus and method for securing ocular tissue and providing surgical tool positioning points.

BACKGROUND

It is often necessary or desirable to secure a patient's eye in place during ocular surgery. For example, it is possible to restore the accommodative power to a presbyopic eye by implanting scleral prostheses within the sclera of the patient's eye. It is also possible to treat glaucoma, ocular hypertension, elevated intraocular pressure, or other eye disorders by implanting scleral prostheses within the sclera of the patient's eye. During these types of procedures, an incision can be made in the sclera of the eye and extended under the surface of the sclera to form a scleral "tunnel," and a scleral prosthesis can then be placed within the tunnel. Before performing a surgical procedure to implant scleral prostheses or other surgical eye procedure, the patient's eye often needs to be fixated so that the patient's eye does not move during the surgical procedure.

SUMMARY

This disclosure provides an apparatus and method for securing ocular tissue and providing surgical tool positioning points.

In a first embodiment, an ocular fixation device includes a body configured to be placed on an eye and multiple tine assemblies configured to secure the body to the eye and to release the body from the eye. The body includes multiple corners and multiple sides, where each corner includes a passage through the corner and each side connects an adjacent pair of the corners. Each tine assembly includes a twist pick configured to be inserted through one of the passages of one of the corners of the body. Bottom surfaces of the sides of the body are raised relative to bottom surfaces of the corners of the body such that the bottom surfaces of the sides are spaced apart from the eye when the bottom surfaces of the corners are resting on the eye. Each of at least one side of the body includes multiple openings configured to allow manipulation of a position of the body and a groove configured to receive a projection from a surgical tool in order to position the surgical tool on the eye.

In a second embodiment, a system includes a surgical tool and an ocular fixation device. The surgical tool is configured to perform a surgical operation on an eye, and the surgical tool includes a projection. The ocular fixation device includes a body configured to be placed on the eye and multiple tine assemblies configured to secure the body to the eye and to release the body from the eye. The body includes multiple corners and multiple sides, where each corner includes a passage through the corner and each side connects an adjacent pair of the corners. Each tine assembly includes a twist pick configured to be inserted through one of the passages of one of the corners of the body. Bottom surfaces of the sides of the body are raised relative to bottom surfaces of the corners of the body such that the bottom surfaces of the sides are spaced apart from the eye when the bottom surfaces of the corners are resting on the eye. Each of at least one side of the body includes multiple openings configured to allow manipulation of a position of the body and a groove configured to receive the projection of the surgical tool in order to position the surgical tool on the eye.

In a third embodiment, an ocular fixation device includes a body configured to be placed on an eye and multiple tine assemblies configured to secure the body to the eye and to release the body from the eye. The body includes multiple corners and multiple sides, where each corner includes a passage through the corner and each side connects an adjacent pair of the corners. Each tine assembly includes a twist pick configured to be inserted through one of the passages of one of the corners of the body. Bottom surfaces of the sides of the body are raised relative to bottom surfaces of the corners of the body such that the bottom surfaces of the sides are spaced apart from the eye when the bottom surfaces of the corners are resting on the eye. Each side of the body further includes (i) multiple openings configured to allow manipulation of a position of the body and (ii) a groove configured to receive a projection from a surgical tool in order to position the surgical tool on the eye. Each corner of the body further includes (i) a surface on which a head of the associated twist pick is able to rest, (ii) a projection extending above and partially over the surface to define a recess or second groove (where the head of the associated twist pick includes a tapered edge configured to fit within the recess or second groove), and (iii) a pointed inner edge that points inward towards an interior of the ocular fixation device (where the pointed inner edges of opposite corners of the body point towards each other). The passages are slanted in different directions relative to a central axis of the body such that the twist picks, once inserted into the passages, angle towards each other below the body and away from each other above the body.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

FIGS. 1 through 14, described below, and the various embodiments used to describe the principles of the present invention in this patent document are by way of illustration only and should not be construed in any way to limit the scope of the invention. Those skilled in the art will understand that the principles of the present invention may be implemented in any type of suitably arranged device or system.

As noted above, it is often necessary or desirable to secure a patient's eye in place during ocular surgery. For example, it is possible to restore the accommodative power to a presbyopic eye or to treat glaucoma, ocular hypertension, elevated intraocular pressure, or other eye disorders by implanting scleral prostheses within the sclera of the patient's eye. During these types of surgical procedures, an incision can be made in the sclera of the eye and extended under the surface of the sclera to form a scleral "tunnel," and a scleral prosthesis can then be placed within the tunnel. Before performing a surgical eye procedure, the patient's eye often needs to be fixated so that the patient's eye does not move during the surgical procedure.

This disclosure provides an ocular fixation device that can be secured to ocular tissue of a patient's eye in order to fixate the patient's eye while providing positioning points for a surgical tool. The ocular fixation device includes a body that can be secured to a patient's eye using multiple tine assemblies. Each tine assembly includes a twist pick having one or more tines, prongs, or other teeth that can be rotated into and out of a patient's ocular tissue in order to respectively secure and release the patient's ocular tissue. Thus, the tine assemblies can be used to secure the body of the ocular fixation device to the patient's eye and to release the body of the ocular fixation device from the patient's eye. The body of the ocular fixation device can also be engaged with a surgical tool in order to properly position the surgical tool relative to the patient's eye. As a result, the ocular fixation device helps to restrain movement of the patient's eye during a surgical procedure, thereby providing ocular fixation. The ocular fixation device also helps to support proper positioning of a surgical tool during the surgical procedure.

Figure 1:
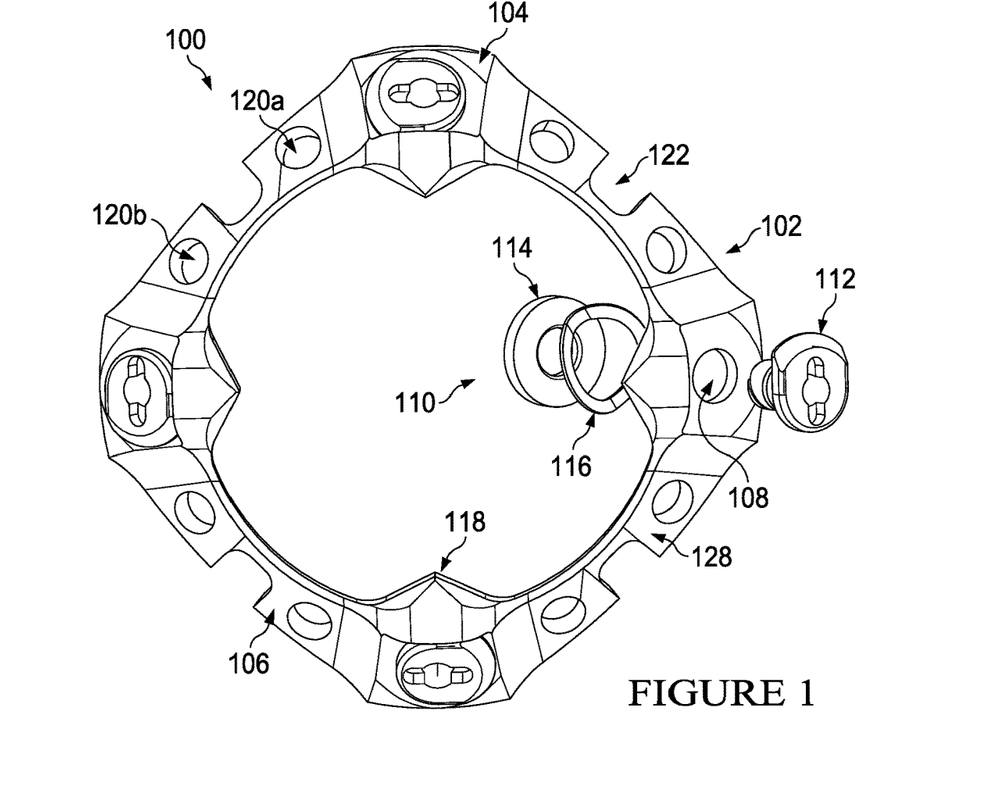
FIGS. 1 through 7 illustrate an example ocular fixation device in accordance with this disclosure.
Figure 2:
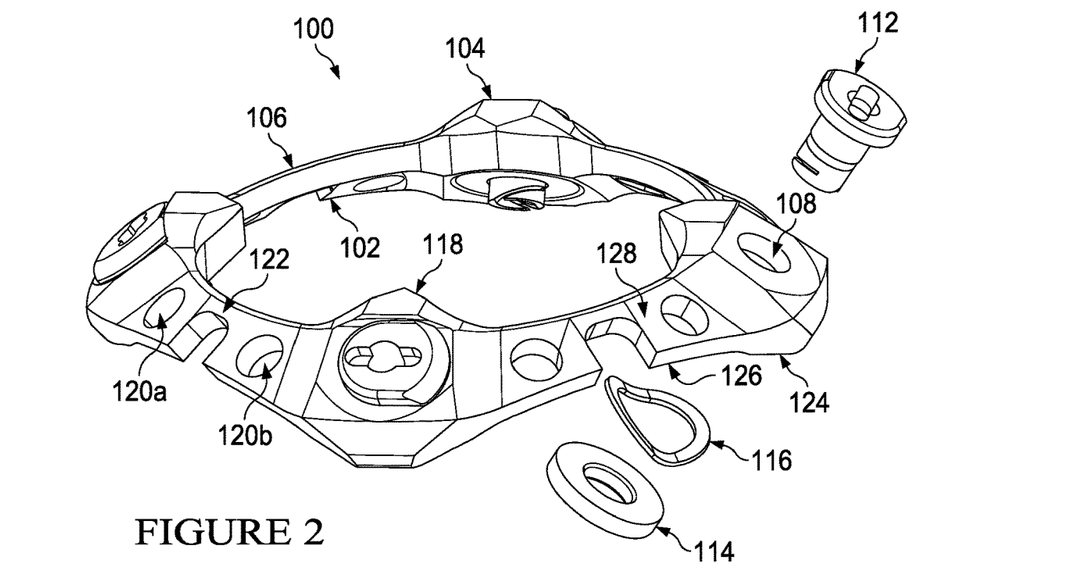
Figure 3:
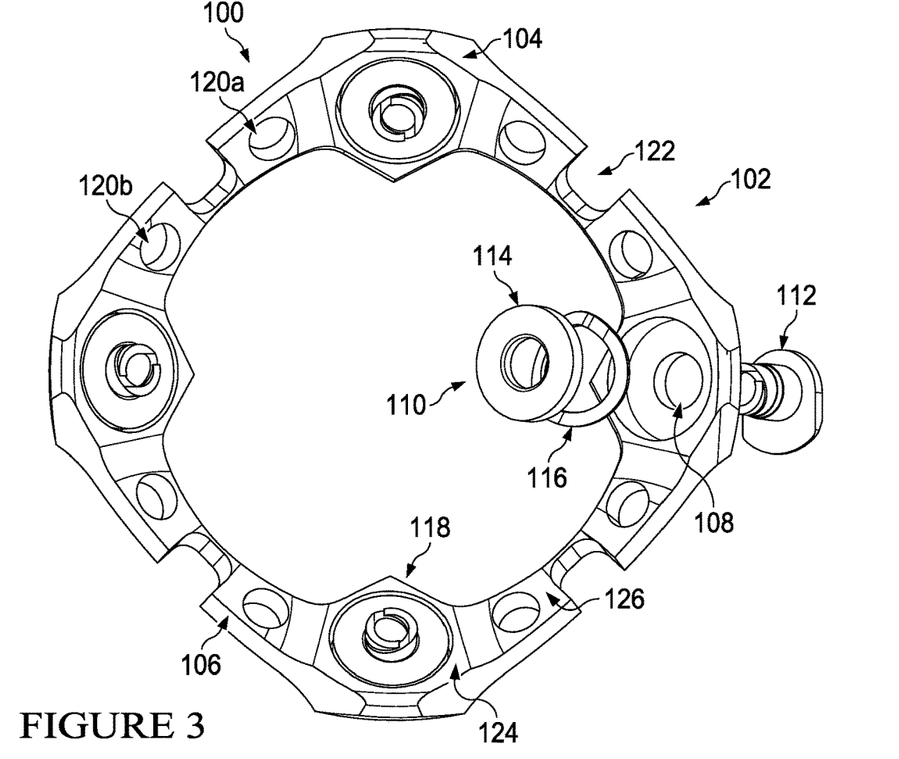
Figure 4:
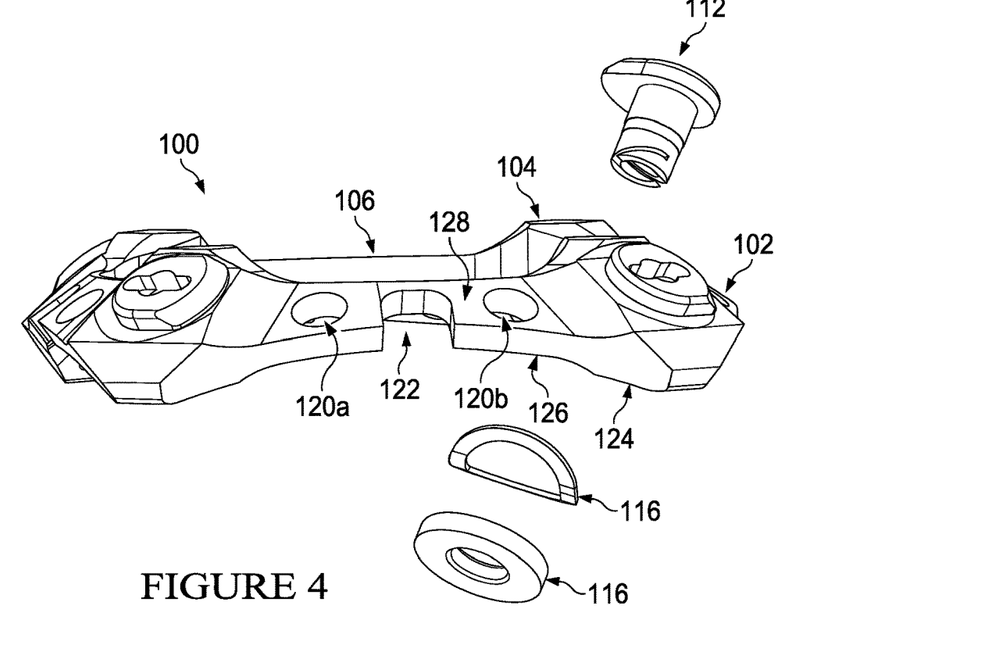
Figure 5:
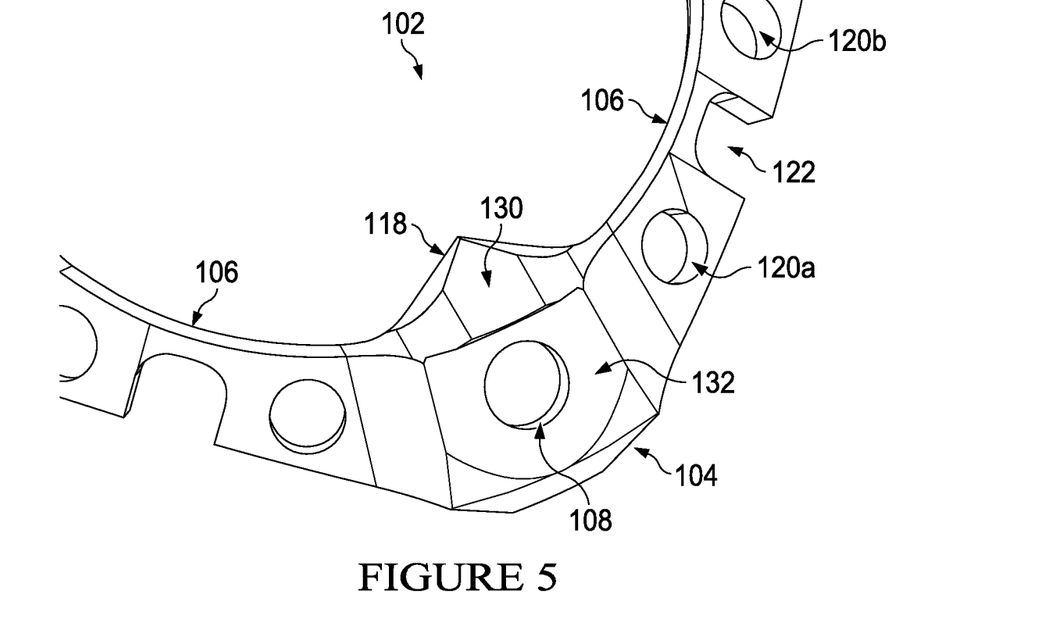
Figure 6:
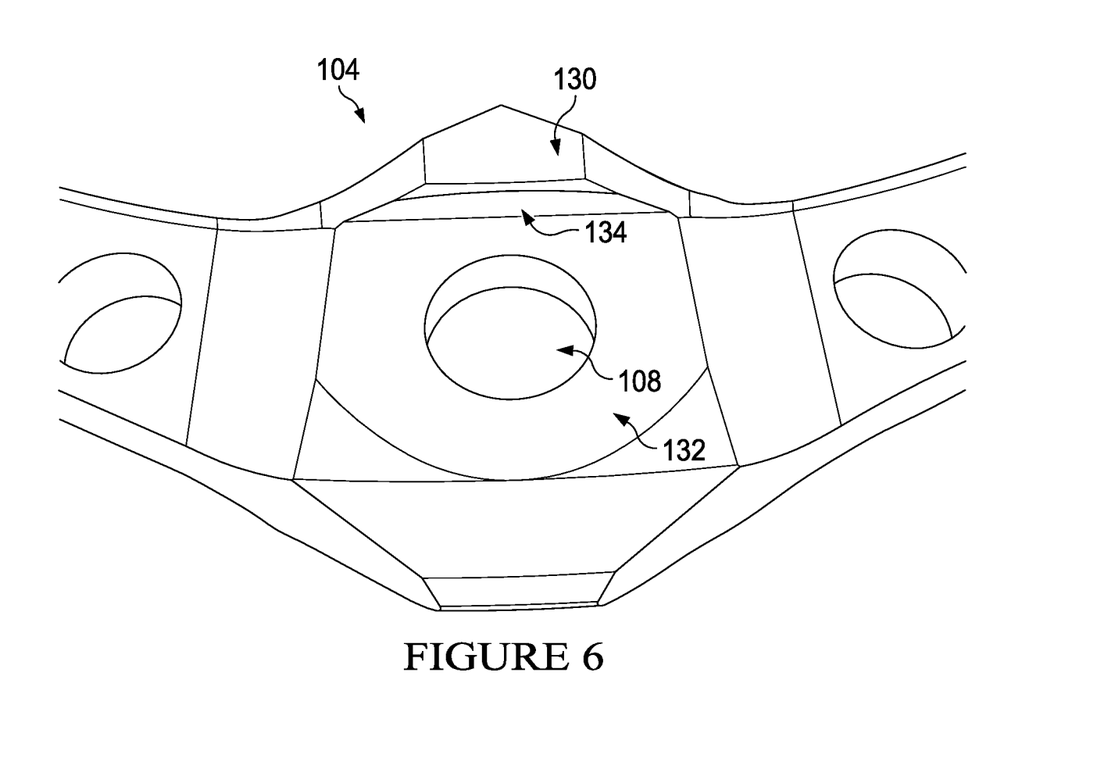
Figure 7:
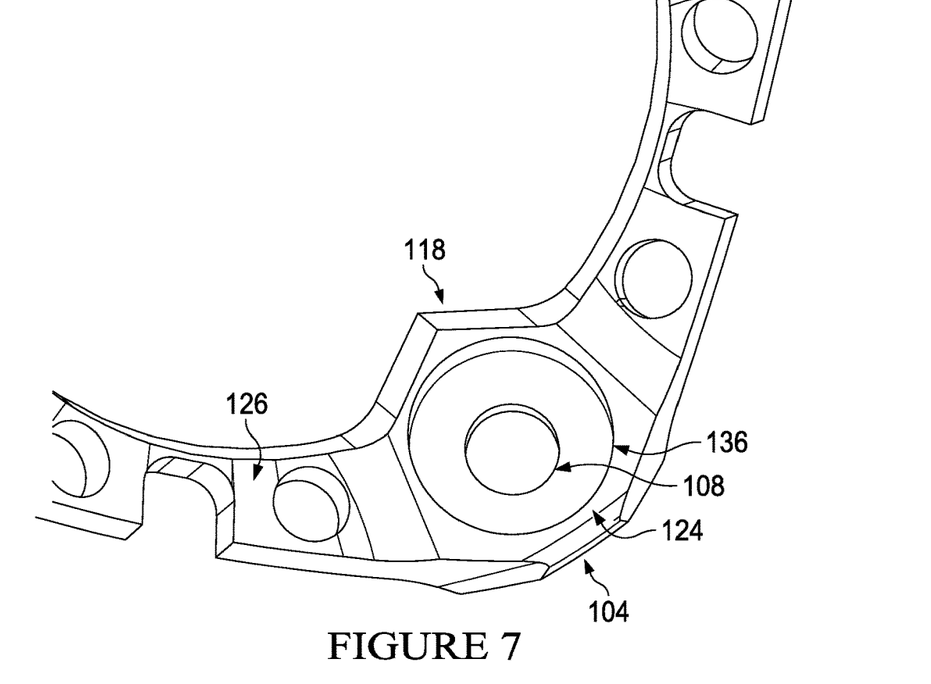

FIGS. 1 through 7 illustrate an example ocular fixation device 100 in accordance with this disclosure. In particular, FIG. 1 illustrates a top view of the ocular fixation device 100, FIG. 2 illustrates a top perspective view of the ocular fixation device 100, FIG. 3 illustrates a bottom view of the ocular fixation device 100, and FIG. 4 illustrates a side perspective view of the ocular fixation device 100. Also, FIGS. 5 and 6 illustrate enlarged top views of portions of the ocular fixation device 100, and FIG. 7 illustrates an enlarged bottom view of a portion of the ocular fixation device 100.

As shown in FIGS. 1 through 4, the ocular fixation device 100 includes a body 102 that is configured to be placed onto the outer surface of a patient's eye. When viewed from the top or bottom, the body 102 is annular and extends along a perimeter of the ocular fixation device 100, with empty space in the interior of the ocular fixation device 100. In this example, the body 102 appears generally square with four corners 104 and four sides 106 connecting the corners 104. Stated differently, the body 102 includes four corners 104 arranged in a square or other grid, and four sides 106 connect the four corners 104. Each side 106 here connects two adjacent corners 104 of the body 102. While generally square, the corners 104 of the body 102 here are rounded, and the sides 106 of the body 102 are curved or arched outward somewhat. However, the corners 104 of the body 102 need not be rounded, and/or the sides 106 of the body 102 may be straight rather than curved.

Each corner 104 of the body 102 includes a passage 108, which passes from a top surface of the corner 104 to a bottom surface of the corner 104. Each passage 108 is used in conjunction with a tine assembly 110, and the tine assemblies 110 are used to secure the body 102 to and release the body 102 from ocular tissue of a patient's eye. Each passage 108 here is generally circular, and each passage 108 here is angled relative to a central axis through the middle of the body 102. More specifically, the passages 108 are angled so that the tine assemblies 110 are angled away from each other along the top of the body 102 and angled towards each other along the bottom of the body 102. However, the passages 108 may have any other suitable form.

Each tine assembly 110 includes a twist pick 112, which represents a bolt- or screw-type structure with a head, shaft, and one or multiple tines, prongs, or other teeth at an end of the shaft. Rotation of each twist pick 112 in one direction causes the one or more teeth of the twist pick 112 to enter into the ocular tissue of a patient's eye, thereby securing the body 102 to the patient's eye. Rotation of each twist pick 112 in the opposite direction causes the one or more teeth of the twist pick 112 to exit the ocular tissue of the patient's eye, thereby releasing the body 102 from the patient's eye.

A portion of the shaft of each twist pick 112 can pass through the passage 108 in the associated corner 104 of the body 102. A retaining washer 114 can be placed around the shaft of the twist pick 112 after the shaft has been inserted through the associated passage 108, thereby helping to retain the twist pick 112 in the passage 108. A beveled or conical washer 116 may optionally be used to apply spring force between the retaining washer 114 and the bottom surface of the corner 104 of the body 102, which can help to bias the twist pick 112 downward in the passage 108 and reduce inadvertent turning or release of the twist pick 112.

Each corner 104 of the body 102 also includes an inner edge 118, which can point inward towards an interior of the ocular fixation device 100. In this example, the four corners 104 of the body 102 include four pointed inner edges 118, and the inner edges 118 of each pair of opposite corners 104 point towards each other. Among other things, the pointed inner edges 118 of the corners 104 can be used to help align the body 102 of the ocular fixation device 100 on a patient's eye. For instance, a mark might be placed on a patient's eye at the "12:00" position, and the pointed inner edge 118 of one corner 104 of the body 102 may be placed so that the point of the inner edge 118 is on or pointing at the 12:00 mark. The other three pointed inner edges 118 of the other three corners 104 may then be used to help center the body 102 of the ocular fixation device 100 on the patient's eye, such as when a surgeon or other personnel position the body 102 so that the inner edges 118 all point towards a center of the patient's cornea or pupil. Of course, other mechanisms may also be used to properly position the body 102 on a patient's eye.

Each side 106 of the body 102 here includes a pair of openings 120a-120b and a groove 122. Each groove 122 may be positioned between the openings 120a-120b in the associated side 106 of the body 102, and each groove 122 may generally be positioned at or near the middle of the side 106. Each pair of openings 120a-120b represents a location where a surgeon or other personnel may grasp the body 102 of the ocular fixation device 100 using forceps or other tool. This helps to allow for easy manipulation of the body 102, such as when placing the body 102 of the ocular fixation device 100 on a patient's eye. Each of the openings 120a-120b may extend completely through the associated side 106 of the body 102, such as from a top surface of the side 106 to a bottom surface of the side 106. Note that while the openings 120a-120b here are shown as circular openings, each opening 120a-120b may have any other suitable shape. Also note that while convenient to have openings 120a-120b along all sides 106 of the body 102, the body 102 may lack openings 120a-120b along one or more sides 106. Further note that the passages 108 here may be positioned along a path extending along the openings 120a-120b and grooves 122 of the sides 106.

Each groove 122 is configured to receive a corresponding projection (such as a "tongue") from a surgical tool in order to properly position the surgical tool on a patient's eye. Since the body 102 in this example includes four sides 106 with four grooves 122, the ocular fixation device 100 provides four different positioning points for a surgical tool on the patient's eye. Of course, if fewer positioning points are needed, the body 102 may lack a groove 122 along one or more sides 106. Each groove 122 here narrows the width of the corresponding side 106 of the body 102 without extending completely through the width of the corresponding side 106. Note that while the grooves 122 here are shown as square or rectangular grooves with rounded corners, each groove 122 may have any other suitable shape.

As can be seen here, the body 102 is designed to be placed onto and rest on the outer surface of a patient's eye, such as when bottom surfaces 124 of the corners 104 of the body 102 are slanted and configured to lie on a sclera of the patient's eye. The sclera represents the tough outer white portion of the patient's eye. Thus, the bottom surfaces 124 of each pair of opposite corners 104 are mirror images of each other and angle away from the central axis through the middle of the body 102 in opposite directions. When placed on a patient's eye, a portion of the patient's cornea may extend into the body 102 between the corners 104 of the body 102 and between the sides 106 of the body 102. The cornea represents the clear front portion of the eye through which light passes to enter into the eye.

As shown in FIGS. 2 and 4, bottom surfaces 126 of the sides 106 of the body 102 are curved, arched, or otherwise raised (relative to the bottom surfaces 124 of the corners 104) so that the bottom surfaces 126 of the sides 106 remain spaced apart from the patient's eye after the body 102 is placed on the patient's eye. This separation allows empty space to exist between the bottom surfaces 126 of the sides 106 of the body 102 and the patient's eye. Among other things, this space permits a surgeon or other personnel to cut the conjunctiva of the patient's eye (which is the mucous membrane covering the front of the patient's eye) and to push a portion of the conjunctiva underneath the nearby side 106 of the body 102. This may allow, for example, the conjunctiva to be easily moved out of the way so that an incision or other operation may be performed on the patient's eye. The conjunctiva can then be repositioned on the patient's eye once the incision has been formed or some other operation has been performed (such as inserting a scleral prosthesis into the incision). The ability to allow the conjunctiva to be cut and easily moved (rather than removed) can help to facilitate faster recovery for the patient. Top surfaces 128 of the corners 104 and sides 106 of the body 102 face away from the central axis of the body 102.

As shown in FIGS. 5 and 6, each corner 104 of the body 102 includes a projection 130 that extends upward and partially over a surface 132 on which a head of a twist pick 112 can rest. The projection 130 is spaced apart from the surface 132 of the corner 104 to define a groove or recess 134, which represents empty space between the bottom of the projection 130 and the surface 132 of the corner 104. The groove or recess 134 can receive part of a twist pick 112 after the twist pick 112 has been rotated to secure the body 102 to a patient's eye. This can help to hold the twist pick 112 in place and prevent unintended rotation of the twist pick 112. Note that the surface 132 of the corner 104 shown here is generally flat, although the surface 132 may be recessed somewhat relative to nearby portions of the body 102 if desired. This may allow, for instance, part of the head of a twist pick 112 to be recessed along the surface 132.

As shown in FIG. 7, a recess 136 may be formed in the bottom surface 124 of each corner 104 of the body 102. Each recess 136 may be sized and shaped to receive the retaining washer 114 and the beveled or conical washer 116 of the associated tine assembly 110. Among other things, this may allow the bottom surface 124 of each corner 104 to sit on the outer surface of a patient's eye, even when the washers 114, 116 are positioned along the shafts of the twist picks 112 in the tine assemblies 110.

During use, the body 102 may be placed on the outer surface of a patient's eye, and the twist picks 112 may be independently rotated (such as by about 180° each) to attach the ends of the twist picks 112 to the patient's ocular tissue. The ocular fixation device 100 can be sized such that the teeth of the twist picks 112 are secured to and release ocular tissue at or near the limbus of the patient's eye. This region of the eye may be well-suited for this type of procedure as it heals rapidly. However, the ocular fixation device 100 could have any other suitable size or shape.

Once attached to the patient's eye, a surgical tool may be placed up against the body 102 and used to perform some type of surgical operation, such as the creation of a scleral pocket/tunnel or other incision. As noted above, prior to using the surgical tool, a surgeon or other personnel may optionally cut the conjunctiva of the patient's eye and push or otherwise reposition part of the conjunctiva under the body 102, such as into or through the space between the patient's eye and the bottom surface 126 of a side 106 of the body 102. When being used to form incisions for implanting scleral prostheses, each scleral prosthesis can be inserted into a scleral pocket/tunnel after formation of the scleral pocket/tunnel and prior to repositioning of the conjunctiva.

Once the surgical procedure is completed, the twist picks 112 may be independently rotated (such as by about 180° each in the opposite direction) to release the ends of the twist picks 112 from the patient's ocular tissue. At that point, the body 102 can be removed from the patient's eye. If the same surgical procedure or a different surgical procedure is to be performed on the patient's other eye, the body 102 may then be attached to, used with, and released from the patient's other eye.

The body 102 of the ocular fixation device 100 may be fabricated using any suitable material(s), such as any suitable metals, ceramics, and synthetic resins. Suitable metals may include titanium, gold, platinum, stainless steel, tantalum, and various other surgically-acceptable alloys. Suitable ceramics may include crystalline and vitreous materials such as porcelain, alumina, silica, silicon carbide, and high-strength glasses. Suitable synthetic resins may include physiologically-inert materials such as poly(methyl methacrylate), polyethylene, polypropylene, poly(tetrafluoroethylene), and silicone resins. The body 102 may also be formed using composite materials, such as those incorporating a synthetic resin or other matrix reinforced with fibers of high-strength material like glass fibers, boron fibers, carbon fibers, or alumina fibers. Particular examples of composite materials may include glass-fiber-reinforced epoxy resin, carbon-fiber-reinforced epoxy resin, or carbon-fiber-reinforced carbon (carbon-carbon). The body 102 of the ocular fixation device 100 may also be fabricated using any suitable manufacturing technique, such as additive manufacturing, subtractive manufacturing (like machining or etching), casting, or injection molding.

The twist pick 112 of each tine assembly 110 of the ocular fixation device 100 may also be fabricated using any suitable material(s), such as any suitable metals, ceramics, synthetic resins, and composite materials. The twist pick 112 of each tine assembly 110 may also be fabricated using any suitable manufacturing technique, such as additive manufacturing, subtractive manufacturing (like machining or etching), casting, or injection molding. Each washer 114, 116 of each tine assembly 110 may be fabricated using any suitable material (s) and using any suitable manufacturing technique. In some cases, the retaining washer 114 may be somewhat pliable so that the retaining washer 114 can be selectively placed around the shaft of a twist pick 112 and removed from the shaft of the twist pick 112.

Although FIGS. 1 through 7 illustrate one example of an ocular fixation device 100, various changes may be made to FIGS. 1 through 7. For example, various modifications may be made to the size, shape, and dimensions of the ocular fixation device 100 or to any of its individual components. Also, various additional components may be added to the ocular fixation device 100 according to particular needs. For instance, a clear or other dome may be placed across the central portion of the ocular fixation device 100 to protect the cornea or other portion of the patient's eye.

Figure 8:
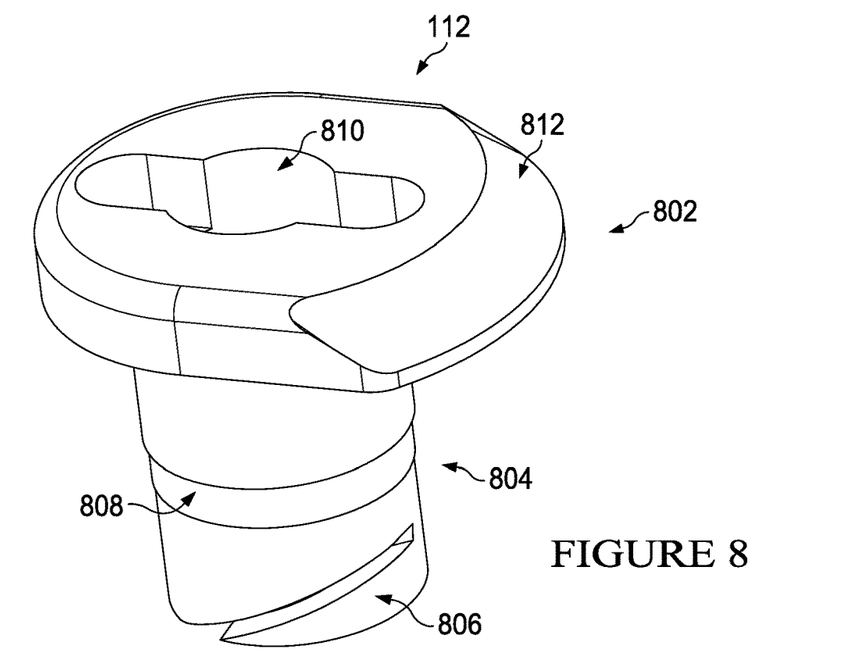
FIGS. 8 through 10 illustrate an example twist pick of a tine assembly for use with an ocular fixation device in accordance with this disclosure.
Figure 9:
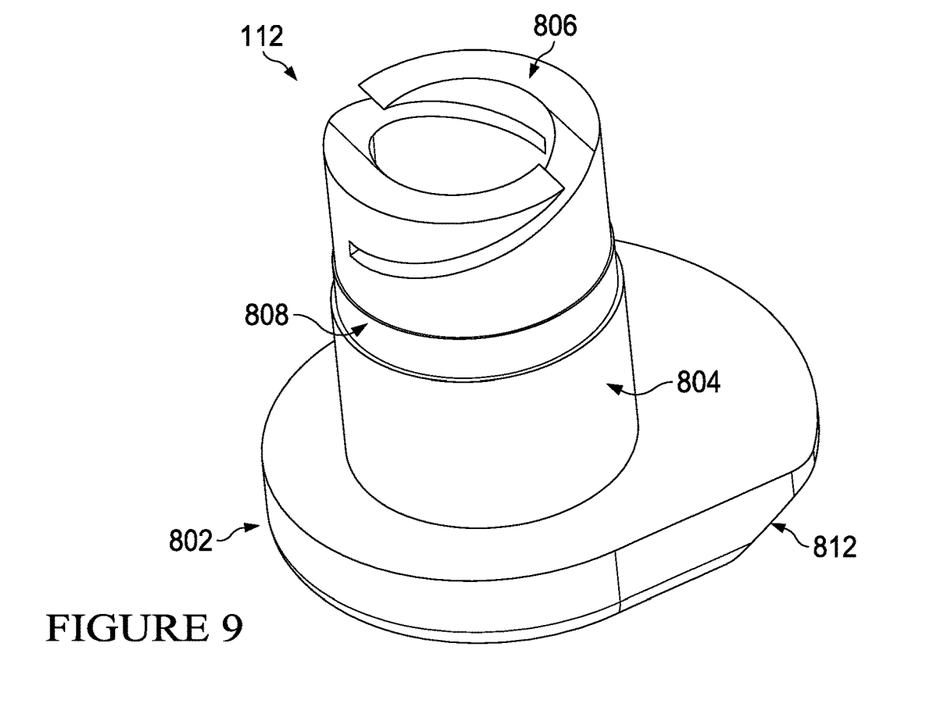
Figure 10:
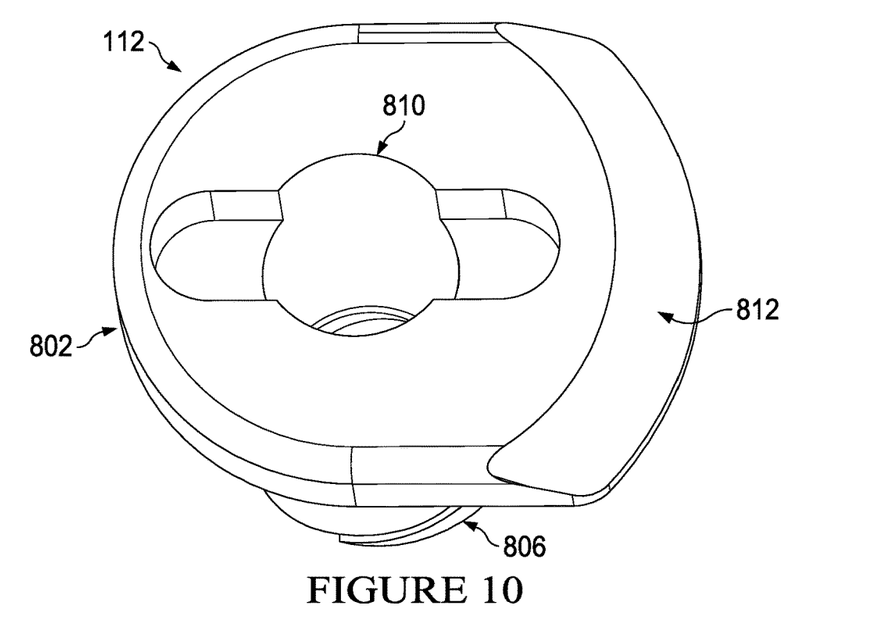

FIGS. 8 through 10 illustrate an example twist pick 112 of a tine assembly 110 for use with an ocular fixation device 100 in accordance with this disclosure. Each tine assembly 110 used with the ocular fixation device 100 may include a twist pick 112 having the form shown in FIGS. 8 through 10, although other twist picks 112 may be used.

As shown in FIGS. 8 through 10, the twist pick 112 includes a head 802, a shaft 804, and multiple tines, prongs, or other teeth 806. The head 802 is attached to or integral with one end of the shaft 804, and the teeth 806 are positioned at or form the opposite end of the shaft 804. The shaft 804 is configured to be inserted through a corresponding passage 108 of the body 102. A shallow groove 808 around the circumference of the shaft 804 may receive an associated retaining washer 114, which can help to retain the twist pick 112 within the corresponding passage 108 of the body 102.

In this example, the teeth 806 are positioned at the lower end of the twist pick 112 and can be used to attach the twist pick 112 to and release the twist pick 112 from ocular tissue (such as scleral tissue) of a patient's eye. In this example, there are two teeth 806 positioned at the end of the shaft 804 of the twist pick 112, although a single tooth 806 or more than two teeth 806 may be used with the twist pick 112. Also in this example, each tooth 806 is curved or arches circumferentially around a central longitudinal axis of the shaft 804, although each tooth 806 may be straight or have any other suitable shape. In some embodiments, the teeth 806 of the twist pick 112 may be formed by machining a shaft 804 that is hollow (or will be machined to be hollow) at least at one end of the shaft 804 in order to form the teeth 806, although any other suitable fabrication technique may be used here.

The head 802 of the twist pick 112 includes a slot 810, which allows a surgeon using a surgical screwdriver or other tool to rotate the twist pick 112. In this example, the slot 810 has a wider central portion and narrower wings or end portions extending from the wider central portion. Also, the wider central portion is generally circular, and the narrower wings or end portions have rounded ends. This may, for example, result from a machining or other operation in which the twist pick 112 is hollowed from the top of the head 802 to the bottom of the shaft 804/teeth 806. However, the slot 810 may have any other suitable form. In some embodiments, the empty space within the slot 810 may join with the hollow space of the shaft 804, which may allow a continuous empty space to extend from the head 802 of the twist pick 112 all the way to the teeth 806 of the twist pick 112. Thus, as shown in FIG. 10, a passage may exist completely through the twist pick 112, although this is not necessarily required.

The head 802 of the twist pick 112 also includes at least one tapered edge 812, which represents a portion of the head 802 in which the thickness of the head 802 decreases. For example, the top surface of the head 802 may angle in a straight or curve downward manner towards a bottom surface of the head 802 in order to reduce the thickness of the head 802 and form the tapered edge 812. The tapered edge 812 can be designed to fit within the groove or recess 134 and fit under the projection 130 in each corner 104 of the body 102. The head 802 of the twist pick 112 may also have an oblong shape, meaning the head 802 of the twist pick 112 is longer in one dimension and shorter in a transverse dimension when the head 802 is viewed straight-on. Because of this shape, the shaft 804 of the twist pick 112 can be inserted into a passage 108 in a corner 104 of the body 102 while the tapered edge 812 of the head 802 is opposite the projection 130 in that corner 104 of the body 102. When desired (such as when securing ocular tissue is desired), the twist pick 112 can be rotated in one direction (such as clockwise in FIG. 8) so that the tapered edge 812 of the twist pick 112 enters the groove or recess 134 and is positioned under the projection 130 in the corner 104 of the body 102. This can help to secure the twist pick 112 in the rotated position and secure the teeth 806 in the ocular tissue of the patient's eye. If the head 802 is somewhat pliant or the space in the groove or recess 134 closely matches the size of the tapered edge 812, the placement of the tapered edge 812 in the groove or recess 134 can help to prevent inadvertent rotation of the twist pick 112. Later (such as when releasing ocular tissue is desired), the twist pick 112 can be rotated in the opposite direction (such as counter-clockwise in FIG. 8) so that the tapered edge 812 of the twist pick 112 exits the groove or recess 134 and is no longer positioned under the projection 130 in the corner 104 of the body 102. This can help to remove the teeth 806 from the ocular tissue of the patient's eye. Note that while a single tapered edge 812 is shown here, it may be possible for multiple sides of the head 802 to have tapered edges.

Note that in some cases, the beveled or conical washer 116 can provide a spring force that helps to push the retaining washer 114 away from the body 102 of the ocular fixation device 100. This can help to keep the head 802 of the twist pick 112 generally positioned up against the surface 132 in the corner 104 of the body 102. As a result, it may be relatively easy for the tapered edge 812 of the twist pick 112 to be rotated into the groove or recess 134 and under the projection 130 in the corresponding corner 104 of the body 102. Of course, the use of the beveled or conical washer 116 is not required, and a surgeon or other personnel may apply downward pressure on the head 802 of the twist pick 112 in order to help ensure that the tapered edge 812 of the twist pick 112 is rotated into the groove or recess 134 and under the projection 130 in the corresponding corner 104 of the body 102.

Again, the twist pick 112 may be fabricated from any suitable material(s) and in any suitable manner. In some embodiments, the twist pick 112 may be fabricated by machining a single piece of material, such as by performing machining operations that (i) form a space through the center of the material to hollow out the shaft 804 and the central portion of the slot 810, (ii) form the narrower wings or end portions of the slot 810, and (iii) form the teeth 806 at the end of the shaft 804. Of course, the twist pick 112 may be fabricated in any other suitable manner, including via the use of multiple parts and/or the use of other fabrication techniques.

Although FIGS. 8 through 10 illustrate one example of a twist pick 112 of a tine assembly 110 for use with an ocular fixation device 100, various changes may be made to FIGS. 8 through 10. For example, various modifications may be made to the size, shape, and dimensions of the twist pick 112 or to any of its individual components.

Figure 11:
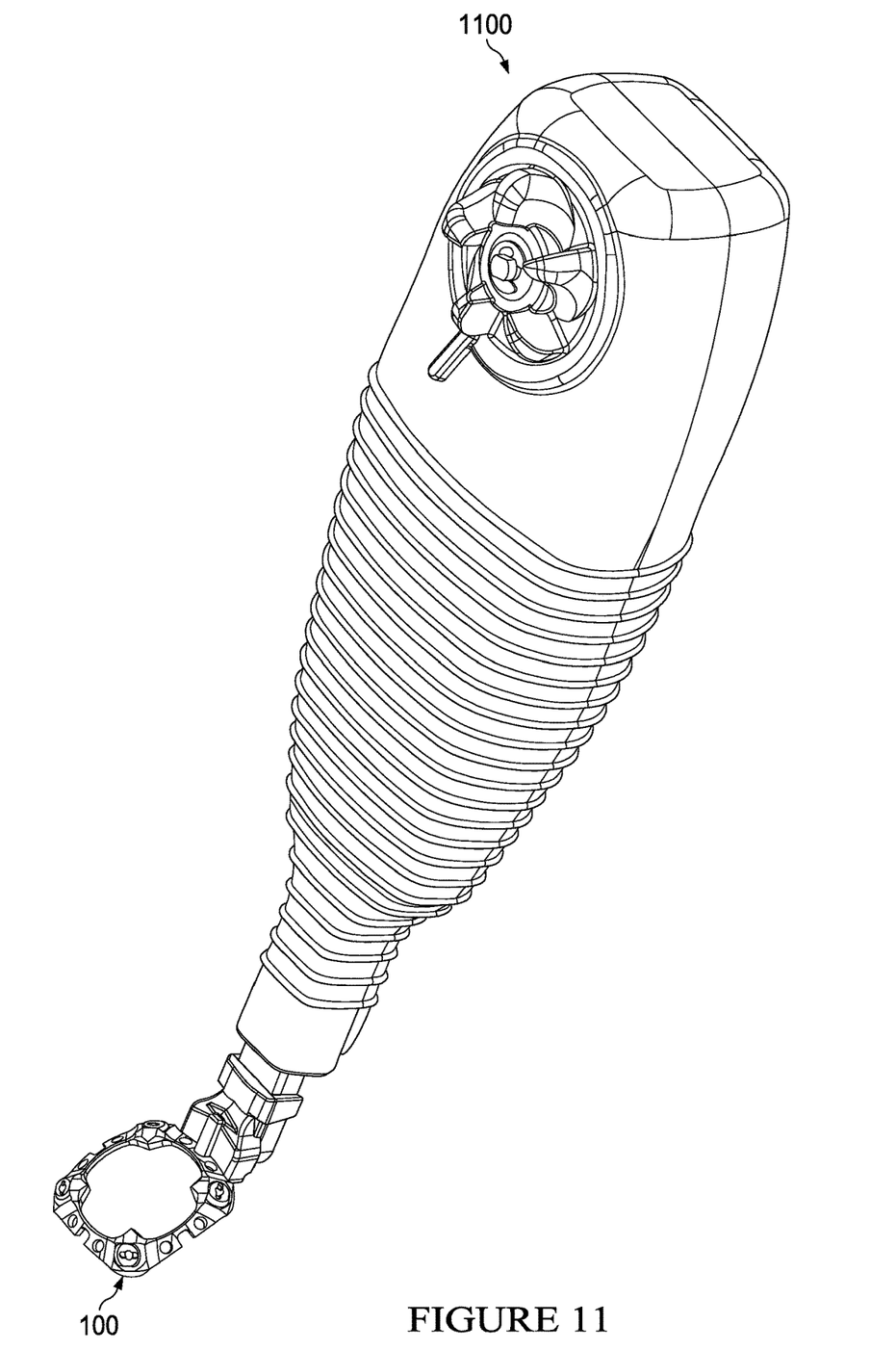
FIGS. 11 through 13 illustrate an example use of an ocular fixation device with a surgical tool in accordance with this disclosure.
Figure 12:
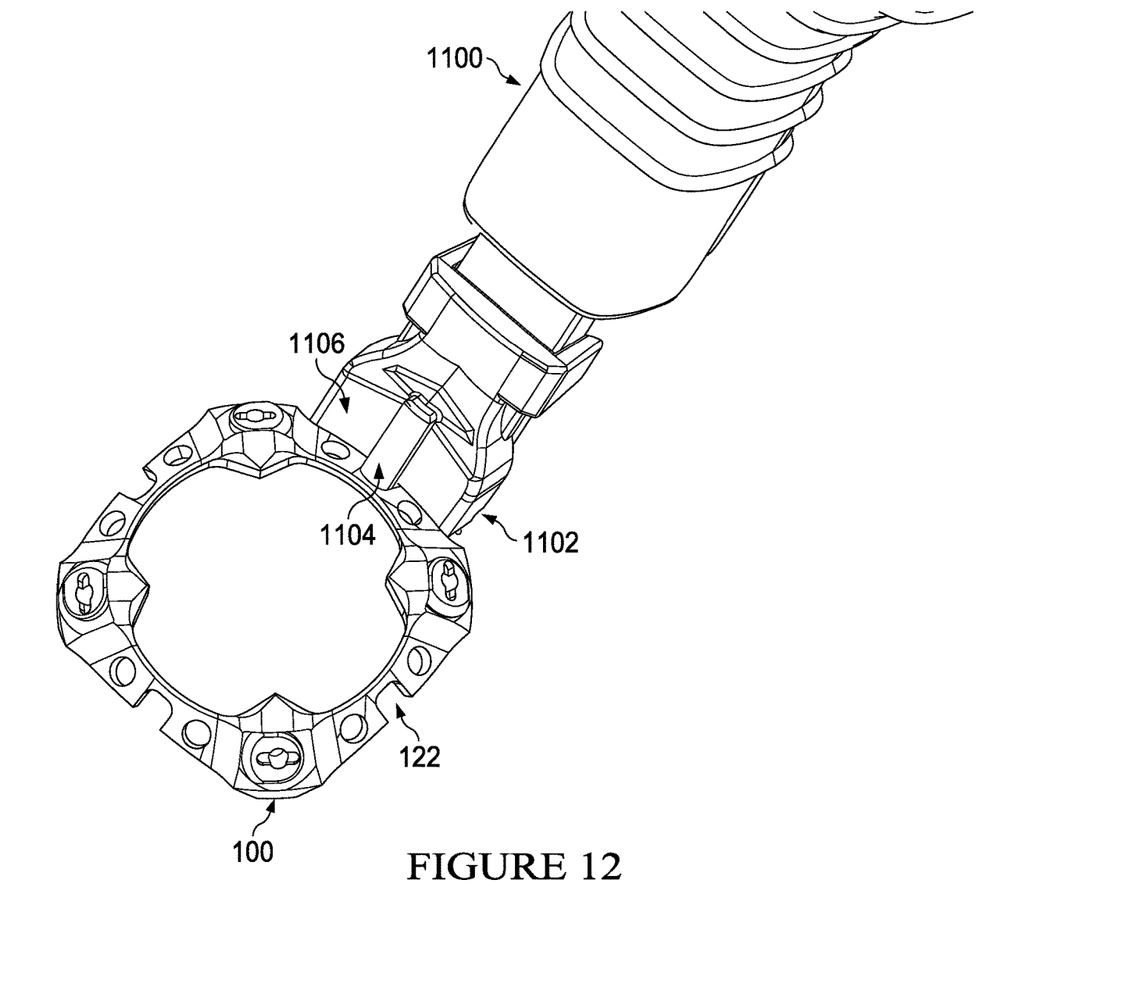
Figure 13:
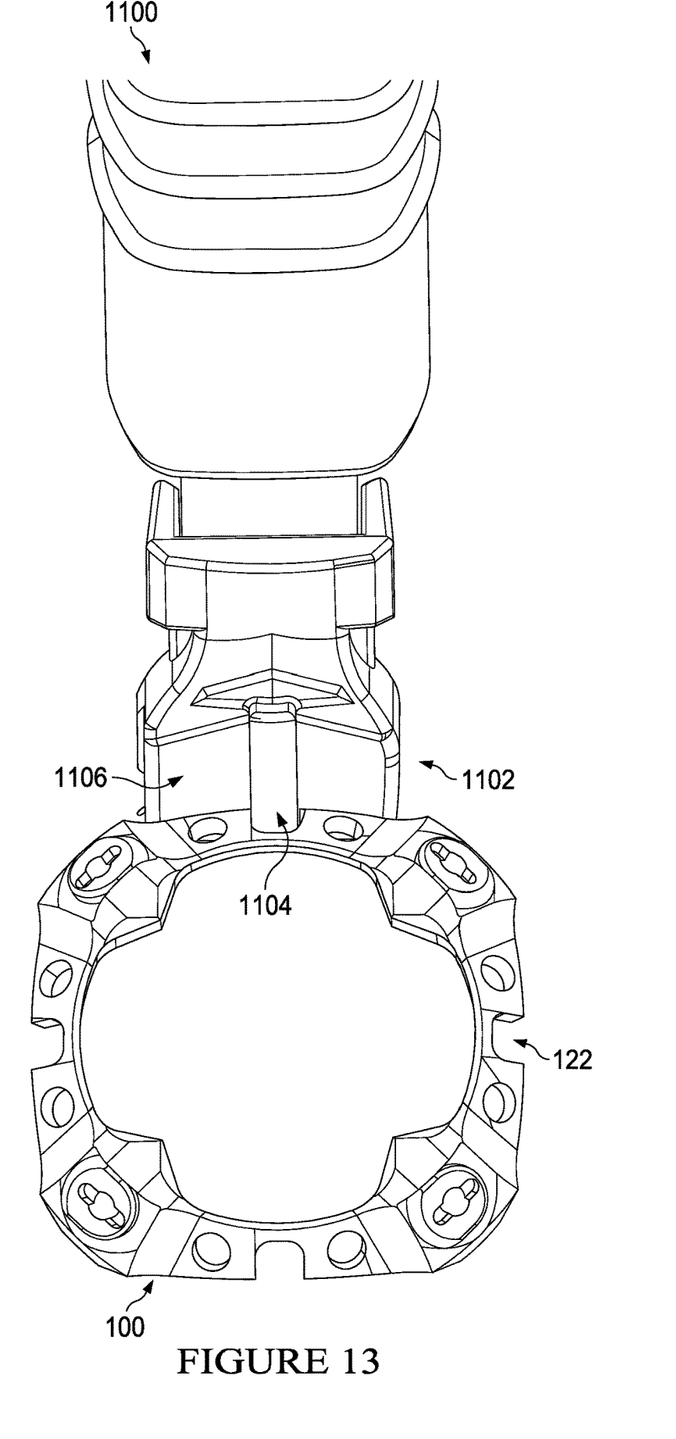

FIGS. 11 through 13 illustrate an example use of an ocular fixation device 100 with a surgical tool 1100 in accordance with this disclosure. As shown in FIGS. 11 through 13, the surgical tool 1100 is used in conjunction with the ocular fixation device 100 to perform a surgical operation on a patient's eye. In some embodiments, the surgical tool 1100 includes a cutting blade that can be moved into and out of the patient's ocular tissue to form an incision (such as a scleral pocket or tunnel). As a particular example, the surgical tool 1100 may include a curved cutting blade connected to a central rotating arm, where the surgical tool 1100 can cause rotation of the central rotating arm in order to rotate the curved cutting blade into and out of the patient's ocular tissue. Of course, any other suitable cutting blade may be used by the surgical tool 1100, or the surgical tool 1100 may include other structures configured to perform at least one other operation on a patient's ocular tissue.

The cutting blade of the surgical tool 1100 here is positioned inside a footplate 1102. The footplate 1102 represents a structure that can be placed on the surface of a patient's eye during use of the surgical tool 1100. In some embodiments, once in the proper position, the surgical blade of the surgical tool 1100 can be rotated, and a portion of the surgical blade passes through the footplate 1102 and into the patient's ocular tissue. In particular embodiments, the footplate 1102 includes one or more slots or other openings that allow the portion of the surgical blade to pass through the footplate 1102 and into (and possibly out of) the patient's ocular tissue. Also, in particular embodiments, the footplate 1102 includes prongs or other mechanisms that help to hold the footplate 1102 in position on the patient's eye during use.

The footplate 1102 here includes a tongue or other projection 1104, as well as a curved or other mating surface 1106. The projection 1104 can fit within each of the grooves 122 along the sides 106 of the ocular fixation device 100, and the mating surface 1106 can contact each of the sides 106 of the ocular fixation device 100 adjacent to the grooves 122. The footplate 1102 can therefore be positioned along each of various sides 106 of the ocular fixation device 100 so that the projection 1104 fits within the groove 122 along that side 106 of the ocular fixation device 100 and the mating surface 1106 contacts that side 106 of the ocular fixation device 100 adjacent to the groove 122. In some cases, four scleral pockets, tunnels, or other incisions are formed in the four quadrants of each of the patient's eyes during a surgical procedure. Thus, the four sides of the ocular fixation device 100 can be used to help properly position the surgical tool 1100 to make incisions in the four quadrants of each eye.

In some embodiments, small incisions may be formed in the conjunctiva of the patient's eye, and a portion of the conjunctiva can be pushed under the ocular fixation device 100 to make room for each incision to be formed. The surgical tool 1100 can be sequentially placed against different sides 106 of the ocular fixation device 100 and used to form multiple incisions in the patient's ocular tissue. The projection 1104 and the mating surface 1106 allow for rapid movement of the surgical tool 1100 to each side 106 of the ocular fixation device 100. As can be seen particularly in FIG. 13, the corners 104 of the ocular fixation device 100 may project somewhat from the sides 106 of the ocular fixation device 100, which can help guide the footplate 1102 into a proper position along each side 106 and help retain the footplate 1102 in place.

Note that various designs of surgical tools 1100 may be used with the ocular fixation device 100. For example, in some instances, the surgical tool 1100 may generally have the form disclosed in U.S. Patent Publication No. 2019/0060124 (which is hereby incorporated by reference in its entirety), except its footplate may be modified as shown here for use with the ocular fixation device 100. Other example surgical tools that might be used here (with modified or added footplates) may include those surgical tools disclosed in U.S. Pat. Nos. 7,189,248; 8,597,318; and 8,771,300 (which are hereby incorporated by reference in their entirety). Of course, any other suitable surgical tool may be used here, as long as the surgical tool has a suitable projection and mating surface or similar structures enabling the surgical tool to be positioned along one or more sides 106 of the ocular fixation device 100.

Also note that, when used to form incisions for receiving ocular implants, any suitable ocular implants may be implanted in the formed incisions. In some embodiments, for example, one or more scleral prostheses may be implanted in each patient's eye being treated. Various examples of scleral prostheses that may be implanted in patients' eyes are disclosed in U.S. Pat. Nos. 6,007,578; 6,280,468; 6,991,650; 7,416,560; 7,927,372; 8,911,496; and U.S. Patent Publication No. 2018/0177588 (which are hereby incorporated by reference in their entirety). Of course, any other suitable ocular implants may be used here, or the surgical tool may be used to perform functions unrelated to the implantation of ocular implants.

Although FIGS. 11 through 13 illustrate one example use of an ocular fixation device 100 with a surgical tool 1100, various changes may be made to FIGS. 11 through 13. For example, the ocular fixation device 100 may be used with any other suitable surgical tool, regardless of whether the surgical tool is used to form scleral pockets/tunnels for receiving scleral implants.

Figure 14:
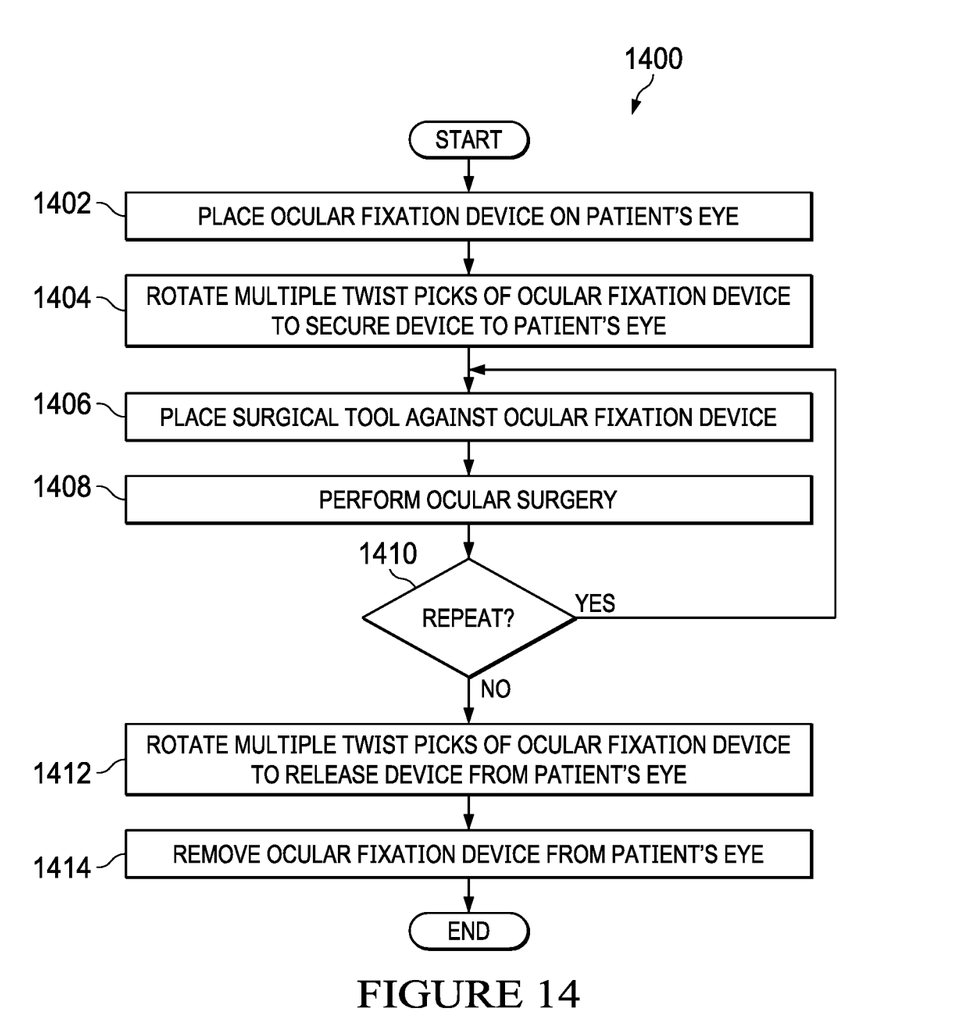
FIG. 14 illustrates an example method for ocular fixation in accordance with this disclosure.

FIG. 14 illustrates an example method 1400 for ocular fixation in accordance with this disclosure. For ease of explanation, the method 1400 of FIG. 14 is described as involving the use of the ocular fixation device 100 and the surgical tool 1100 described above. However, the method 1400 may involve the use of any suitable ocular fixation device designed in accordance with the teachings of this disclosure and with any suitable surgical tool.

An ocular fixation device is placed on a patient's eye at step 1402. This may include, for example, a surgeon or other personnel placing the body 102 of the ocular fixation device 100 on the patient's eye. As a particular example, the surgeon or other personnel may place the tips of forceps within the openings 120a-120b along one side 106 of the body 102 in order to manipulate and properly position the body 102 on the patient's eye. In some cases, the body 102 of the ocular fixation device 100 can be placed on the patient's eye based on at least one marking on the patient's eye and/or based on centering the body 102 on the patient's eye using the pointed inner edges 118 of the body 102.

Multiple twist picks of the ocular fixation device are rotated to secure the body of the ocular fixation device to the patient's eye at step 1404. This may include, for example, the surgeon or other personnel using a surgical screwdriver or other tool to rotate each twist pick 112 (such as about 180°) to cause one or more teeth 806 of each twist pick 112 to enter into the ocular tissue of the patient's eye. This may also include causing a tapered edge 812 of the head 802 of each twist pick 112 to be rotated into the groove or recess 134 and under the projection 130 in the associated corner 104 of the body 102.

A surgical tool is placed against the ocular fixation device at step 1406. This may include, for example, the surgeon or other personnel placing a surgical tool 1100 against one side 106 of the ocular fixation device 100. This may also include the surgeon or other personnel placing a projection 1104 of a footplate 1102 of the surgical tool 1100 within a groove 122 along one side 106 of the ocular fixation device 100 and placing a mating surface 1106 of the footplate 1102 against the side 106 of the ocular fixation device 100 adjacent to the groove 122. Optionally, prior to this step, the surgeon or other personnel may form an incision in the conjunctiva of the patient's eye and reposition a portion of the conjunctiva out of the way (and possibly under the side 106 of the ocular fixation device 100) so that the surgical tool 1100 can be used. An ocular surgical procedure occurs at step 1408. This may include, for example, the surgeon or other personnel using the surgical tool 1100 to form one or more scleral pockets/tunnels or other incisions in scleral tissue or other ocular tissue of the patient's eye. As a particular example, this may include the surgical tool 1100 rotating a curved cutting blade or otherwise moving a cutting blade to form an incision in the scleral tissue or other ocular tissue of the patient's eye. A decision is made whether to repeat the use of the surgical tool at step 1410. If so, the process returns to step 1406, where the surgeon or other personnel can move the surgical tool 1100 to another side 106 of the ocular fixation device 100 and form another incision. Note that during these steps, the surgeon or other personnel may implant one or more scleral prostheses in the patient's eye or perform other surgical operations. This can be done individually (after each incision is formed) or collectively (after all incisions are formed).

Once completed, the twist picks of the ocular fixation device are rotated to release the body of the ocular fixation device from the patient's eye at step 1412. This may include, for example, the surgeon or other personnel using the surgical screwdriver or other tool to rotate each twist pick 112 (such as about 180°) to cause the one or more teeth 806 of each twist pick 112 to exit the ocular tissue of the patient's eye. This may also include causing the tapered edge 812 of the head 802 of each twist pick 112 to be rotated out of the groove or recess 134 and out from under the projection 130 in the associated corner 104 of the body 102. The ocular fixation device is removed from the patient's eye at step 1414. This may include, for example, the surgeon or other personnel removing the body 102 of the ocular fixation device 100 from the patient's eye.

Although FIG. 14 illustrates one example of a method 1400 for ocular fixation, various changes may be made to FIG. 14. For example, while shown as a series of steps, various steps in FIG. 14 may overlap, occur in parallel, occur in a different order, or occur any number of times. Also, any suitable surgical procedure could involve the use of ocular fixation. The surgical procedure may, but need not, involve the implantation of one or more scleral prostheses or other implants or elements into the patient's eye.

It may be advantageous to set forth definitions of certain words and phrases used throughout this patent document. The terms "include" and "comprise," as well as derivatives thereof, mean inclusion without limitation. The term "or" is inclusive, meaning and/or. The phrase "associated with," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. An ocular fixation device comprising:
   a body configured to be placed on an eye, the body comprising multiple corners and multiple sides, each corner comprising a passage through the corner, each side connecting an adjacent pair of the corners; and
   multiple tine assemblies configured to secure the body to the eye and to release the body from the eye, each tine assembly comprising a twist pick configured to be inserted through an associated one of the passages of an associated one of the corners of the body;
   wherein bottom surfaces of the sides of the body are raised relative to bottom surfaces of the corners of the body such that the bottom surfaces of the sides are spaced apart from the eye when the bottom surfaces of the corners are resting on the eye;
   wherein each of at least one side of the body comprises:
      multiple openings configured to allow manipulation of a position of the body; and
      a groove configured to receive a projection from a surgical tool in order to position the surgical tool on the eye; and
   wherein each corner of the body further comprises:
      a surface on which a head of the associated twist pick is able to rest; and
      a second projection extending above and partially over the surface to define a recess or second groove, the head of the associated twist pick comprising a tapered edge configured to fit within the recess or second groove.

2. The ocular fixation device of claim 1, wherein:
   each corner of the body further comprises a pointed inner edge that points inward towards an interior of the ocular fixation device; and
   the pointed inner edges of opposite corners of the body point towards each other.

3. The ocular fixation device of claim 1, wherein, for each side of the body, the groove is positioned between the multiple openings and at a middle of the side.

4. The ocular fixation device of claim 1, wherein each of the twist picks comprises a shaft connected at one end to the head of the twist pick and one or more teeth at another end of the shaft opposite the head, the head further comprising a slot.

5. The ocular fixation device of claim 4, wherein, for each twist pick, the shaft is hollow such that empty space within the slot of the head joins with hollow space of the shaft to form a continuous empty space extending completely through the twist pick.

6. The ocular fixation device of claim 1, wherein the passages are slanted in different directions relative to a central axis of the body such that the twist picks, once inserted into the passages, angle towards each other below the body and away from each other above the body.

7. The ocular fixation device of claim 1, wherein:
the body comprises four corners arranged in a square grid;
the body comprises four sides that are curved; and
the ocular fixation device comprises four tine assemblies.

8. An ocular fixation device comprising:
a body configured to be placed on an eye, the body comprising multiple corners and multiple sides, each corner comprising a passage through the corner, each side connecting an adjacent pair of the corners; and
multiple tine assemblies configured to secure the body to the eye and to release the body from the eye, each tine assembly comprising a twist pick configured to be inserted through an associated one of the passages of an associated one of the corners of the body;
wherein bottom surfaces of the sides of the body are raised relative to bottom surfaces of the corners of the body such that the bottom surfaces of the sides are spaced apart from the eye when the bottom surfaces of the corners are resting on the eye;
wherein each of at least one side of the body comprises:
multiple openings configured to allow manipulation of a position of the body; and
a groove configured to receive a projection from a surgical tool in order to position the surgical tool on the eye;
wherein each tine assembly further comprises a retaining washer and a beveled or conical washer; and
wherein each corner further comprises a recess in the bottom surface of the corner, the recess configured to receive the retaining washer and the beveled or conical washer of the associated tine assembly.

9. The ocular fixation device of claim 8, wherein each corner of the body further comprises:
a surface on which a head of the associated twist pick is able to rest; and
a second projection extending above and partially over the surface to define a second recess or second groove, the head of the associated twist pick comprising a tapered edge configured to fit within the second recess or second groove.

10. A system comprising:
a surgical tool configured to perform a surgical operation on an eye, the surgical tool comprising a projection; and
an ocular fixation device comprising:
a body configured to be placed on the eye, the body comprising multiple corners and multiple sides, each corner comprising a passage through the corner, each side connecting an adjacent pair of the corners; and
multiple tine assemblies configured to secure the body to the eye and to release the body from the eye, each tine assembly comprising a twist pick configured to be inserted through an associated one of the passages of an associated one of the corners of the body;
wherein bottom surfaces of the sides of the body are raised relative to bottom surfaces of the corners of the body such that the bottom surfaces of the sides are spaced apart from the eye when the bottom surfaces of the corners are resting on the eye;
wherein each of at least one side of the body comprises:
multiple openings configured to allow manipulation of a position of the body; and
a groove configured to receive the projection of the surgical tool in order to position the surgical tool on the eye;
wherein each tine assembly further comprises a retaining washer and a beveled or conical washer; and
wherein each corner further comprises a recess in the bottom surface of the corner, the recess configured to receive the retaining washer and the beveled or conical washer of the associated tine assembly.

11. The system of claim 10, wherein:
each corner of the body further comprises a pointed inner edge that points inward towards an interior of the ocular fixation device; and
the pointed inner edges of opposite corners of the body point towards each other.

12. The system of claim 10, wherein, for each side of the body, the groove is positioned between the multiple openings and at a middle of the side.

13. The system of claim 10, wherein each of the twist picks comprises a shaft, a head with a slot at one end of the shaft, and one or more teeth at another end of the shaft opposite the head.

14. The system of claim 13, wherein, for each twist pick, the shaft is hollow such that empty space within the slot of the head joins with hollow space of the shaft to form a continuous empty space extending completely through the twist pick.

15. The system of claim 10, wherein the passages are slanted in different directions relative to a central axis of the body such that the twist picks, once inserted into the passages, angle towards each other below the body and away from each other above the body.

16. The system of claim 10, wherein:
the surgical tool further comprises a footplate configured to be placed on a surface of the eye; and
the footplate comprises the projection and a mating surface configured to be placed against the at least one side of the ocular fixation device while the projection is positioned within the groove of the at least one side of the ocular fixation device.

17. The system of claim 10, wherein the surgical tool is configured to form a scleral pocket or tunnel in the eye.

18. A system comprising:
a surgical tool configured to perform a surgical operation on an eye, the surgical tool comprising a projection; and
an ocular fixation device comprising:
a body configured to be placed on the eye, the body comprising multiple corners and multiple sides, each corner comprising a passage through the corner, each side connecting an adjacent pair of the corners; and
multiple tine assemblies configured to secure the body to the eye and to release the body from the eye, each tine assembly comprising a twist pick configured to be inserted through an associated one of the passages of an associated one of the corners of the body;

wherein bottom surfaces of the sides of the body are raised relative to bottom surfaces of the corners of the body such that the bottom surfaces of the sides are spaced apart from the eye when the bottom surfaces of the corners are resting on the eye;

wherein each of at least one side of the body comprises:
multiple openings configured to allow manipulation of a position of the body; and
a groove configured to receive the projection of the surgical tool in order to position the surgical tool on the eye; and wherein each corner of the body further comprises:
a surface on which a head of the associated twist pick is able to rest; and
a second projection extending above and partially over the surface to define a recess or second groove, the head of the associated twist pick comprising a tapered edge configured to fit within the recess or second groove.

19. The system of claim 18, wherein:
each tine assembly further comprises a retaining washer and a beveled or conical washer; and
each corner further comprises a second recess in the bottom surface of the corner, the second recess configured to receive the retaining washer and the beveled or conical washer of the associated tine assembly.

20. An ocular fixation device comprising:
a body configured to be placed on an eye, the body comprising multiple corners and multiple sides, each corner comprising a passage through the corner, each side connecting an adjacent pair of the corners; and
multiple tine assemblies configured to secure the body to the eye and to release the body from the eye, each tine assembly comprising a twist pick configured to be inserted through an associated one of the passages of an associated one of the corners of the body;

wherein bottom surfaces of the sides of the body are raised relative to bottom surfaces of the corners of the body such that the bottom surfaces of the sides are spaced apart from the eye when the bottom surfaces of the corners are resting on the eye;

wherein each side of the body further comprises (i) multiple openings configured to allow manipulation of a position of the body and (ii) a groove configured to receive a projection from a surgical tool in order to position the surgical tool on the eye;

wherein each corner of the body further comprises (i) a surface on which a head of the associated twist pick is able to rest, (ii) a second projection extending above and partially over the surface to define a recess or second groove, the head of the associated twist pick comprising a tapered edge configured to fit within the recess or second groove, and (iii) a pointed inner edge that points inward towards an interior of the ocular fixation device, the pointed inner edges of opposite corners of the body pointing towards each other; and wherein the passages are slanted in different directions relative to a central axis of the body such that the twist picks, once inserted into the passages, angle towards each other below the body and away from each other above the body.

* * * * *